United States Patent [19]
Broughton et al.

[11] 3,933,822
[45] Jan. 20, 1976

[54] AZAPURINONES

[75] Inventors: Barbara Joyce Broughton, Croydon; Bryan John Large, Ilkley; Stuart Malcolm Marshall, Stanford-le-Hope; David Lord Pain, Upminster; Kenneth Robert Harry Wooldridge, Brentwood, all of England

[73] Assignee: May & Baker Limited, Essex, England

[22] Filed: June 11, 1974

[21] Appl. No.: 478,387

[30] Foreign Application Priority Data
June 12, 1973 United Kingdom............. 27920/73

[52] U.S. Cl............. 260/256.5 R; 424/45; 424/248; 424/251; 424/253; 260/247.1
[51] Int. Cl.².................................. C07D 239/00
[58] Field of Search................................ 260/256.5

[56] References Cited
UNITED STATES PATENTS
3,819,631  6/1974  Broughton et al............. 260/256.4

OTHER PUBLICATIONS
Chemical Abstracts 54:22115g, (1960).

Primary Examiner—Leonard Schenkman
Attorney, Agent, or Firm—Stevens, Davis, Miller & Mosher

[57] ABSTRACT

8-Azapurin-6-ones substituted in the 2-position by a phenyl group carrying in a meta-position a sulphamoyl substituent, and also a hydroxy, alkoxy or alkylthio substituent para with respect to the said sulphamoyl grouping, and pharmaceutically acceptable salts thereof, possess pharmacological properties useful in the treatment of allergic respiratory disorders, for example allergic bronchial asthma.

13 Claims, No Drawings

AZAPURINONES

This invention relates to new therapeutically useful 8-azapurin-6-one derivatives, to a process for their preparation and to pharmaceutical compositions containing them.

In the specifications of our U.S. patent applications Ser. Nos. 207986 now U.S. Pat. No. 3,819,631 patented June 25th 1974 and copending 364425 entitled "Azapurinones" and filed December 14th 1971 and 29th May 1973 respectively there are described the class of new 8-azapurin-6-one derivatives represented by the general formula:

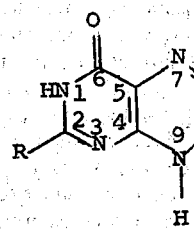

I wherein R represents a phenyl or naphthyl group, which may optionally carry one or more (preferably at most three) substituents selected from halogen (preferably fluorine), chlorine or bromine) atoms and hydroxy, alkyl, phenylalkyl, alkoxy, alkenyloxy, alkynyloxy, alkoxyalkoxy, phenoxy, aralkoxy (e.g. phenylalkoxy), alkylthio, hydroxyalkyl, nitro, alkanesulphonyl, alkanoyl, alkoxycarbonyl, amino, trifluoromethyl and methylenedioxy groups and amino groups substituted by one or two groups selected from alkyl, phenyl, alkanoyl, alkanesulphonyl and arenesulphonyl (e.g. benzenesulphonyl) groups, or R represents a straight- or branched-chain alkenyl or alkynyl group containing from 2 to 6 carbon atoms, a cycloalkyl group containing from 3 to 8 carbon atoms (e.g. cyclohexyl), a straight- or branched-chain alkyl group containing from 2 to 10 carbon atoms (preferably isopropyl, butyl or isobutyl), or a straight- or branched-chain alkyl group containing from 1 to 10 carbon atoms (preferably methyl or ethyl) carrying one or more (preferably at most two) substituents selected from halogen atoms, hydroxy groups, cycloalkyl groups containing from 3 to 8 carbon atoms (preferably cyclohexyl), straight- or branched-chain alkoxy groups containing from 1 to 6 carbon atoms, and phenyl groups optionally carrying one or more (preferably at most two) substituents selected from halogen atoms and straight- or branched-chain alkyl and alkoxy groups containing from 1 to 6 carbon atoms, hydroxy groups, and phenylalkoxy (e.g. benzyloxy) groups in which the alkoxy moiety contains 1 to 6 carbon atoms, and pharmaceutically acceptable salts thereof.

In those specifications it is stated that, when R represents a substituted phenyl or substituted naphthyl group, alkyl groups and alkyl portions of phenylalkyl, alkylthio, aralkoxy, alkanoyl, alkanesulphonyl, hydroxyalkyl and alkoxycarbonyl substituents contain from 1 to 6 carbon atoms, each alkyl portion of an alkoxyalkoxy substituent contains from 1 to 6 carbon atoms; alkoxy substituents contain from 1 to 10 carbon atoms; alkenyloxy and alkynyloxy substituents contain 2 to 10 carbon atoms and alkyl and alkanoyl groups on amino substituents, and alkane portions of alkanesulphonyl groups on amino substituents, contain from 1 to 6 carbon atoms; phenoxy substituents, and phenyl groups on amino substituents may carry one or more substituents selected from halogen (e.g. fluorine, chlorine or bromine) atoms, and alkyl and alkoxy groups containing from 1 to 6 carbon atoms; aryl (e.g. phenyl) portions of aralkoxy substituents may carry one or more substituents selected from halogen (e.g. fluorine, chlorine or bromine) atoms, alkyl and alkoxy groups containing from 1 to 6 carbon atoms and nitro groups; and arene (e.g. benzene) portions of arenesulphonyl groups on amino substituents may carry one or more alkyl groups containing from 1 to 6 carbon atoms (e.g. methyl). It is further stated that the carbon atoms in the alkyl, alkoxy, alkanoyl, alkane, alkenyloxy and alkynyloxy groups or moieties may be in a straight- or branched-chain.

It is pointed out in our above-mentioned specifications that the compounds of formula I exhibit tautomerism such that each of the hydrogen atoms depicted as residing on the nitrogen atoms in the 1- and 9-positions may reside on any of the nitrogen atoms in the 1-, 3-, 7-, 8- and 9-positions or on the oxygen atom connected to the carbon atom in the 6-position, and that all the forms thus described may be present to a greater or lesser degree and are in a state of dynamic equilibrium with each other. Furthermore, in certain cases the substituent R contributes to optical and/or stereoisomerism. All such forms are embraced by the invention described in our aforementioned specification.

According to a feature of the invention described in our aforementioned specifications, compounds of formula I are prepared from compounds of the general formula:

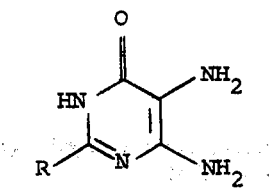

II (wherein R is as hereinbefore defined) by the action of a source of nitrous acid, for example a nitrite of an alkali metal, e.g. sodium nitrite or potassium nitrite, together with an acid, for example dilute aqueous hydrochloric acid, preferably as the reaction medium, at a temperature near or below the ambient temperature, for example between 0° and 30°C.

Compounds of formula II may be prepared, for example, by the reduction of compounds of the general formula:

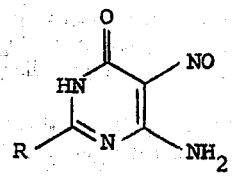

III (wherein R is as hereinbefore defined) with suitable reducing agents, for example sodium dithionite in water or an aqueous lower alkanol, e.g. aqueous ethanol, optionally in the presence of a base, e.g. triethylamine.

Compounds of formula III may be prepared, for example, by the reaction of compounds of the general formula:

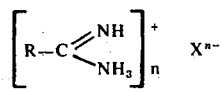 IV (wherein R is as hereinbefore defined, X$^{n-}$ represents the anion of a suitable acid, for example an inorganic acid (e.g. hydrochloric acid), or a strong organic acid (e.g. methanesulphonic or toluene-p-sulphonic acid), and n is the basicity of that acid) with an alkyl α-oximinocyanoacetate, for example ethyl α-oximinocyanoacetate, in the presence of a lower alkoxide of an alkali metal in a lower alkanol, for example sodium ethoxide in ethanol, preferably at an elevated temperature, advantageously at the reflux temperature of the reaction mixture.

Compounds of formula IV may be prepared by the action of acids of the general formula H$_n$X (wherein X and n are as hereinbefore defined) on compounds of the general formula:

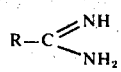 V (wherein R is as hereinbefore defined), which may themselves be prepared, for example, by the catalytic hydrogenation of compounds of the general formula:

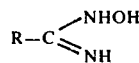 VI (wherein R is as hereinbefore defined), preferably using Raney nickel as catalyst.

Compounds of formula VI may be prepared by the reaction of hydroxylamine hydrochloride with compounds of the general formula:
 RCN VII (wherein R is as hereinbefore defined) with a basic catalyst in a suitable solvent, for example sodium carbonate in aqueous ethanol, sodium hydride in ethyl cellosolve, or triethylamine, which may also act as solvent.

The 8-azapurin-6-one derivatives of general formula I described in our aforementioned specification possess valuable pharmacological properties, in particular properties of value in the treatment of respiratory disorders manifested by the interaction of tissue-fixed antibodies with specific antigens, such as allergic bronchial asthma.

It has now been found as a result of further research and experimentation that when R in general formula I represents a phenyl group substituted in the meta-position by a sulphamoyl grouping the hitherto unknown compounds exhibit similar valuable pharmacological properties to the 8-azapurin-6-one derivatives of general formula I.

The present invention accordingly provides compounds of the general formula:

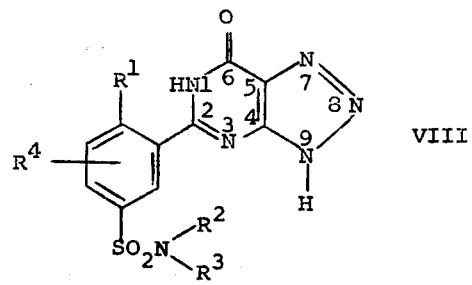 VIII

[wherein R$^1$ represents a hydroxy group, a straight- or branched-chain alkoxy or alkylthio group containing from 1 to 10, preferably from 1 to 3, carbon atoms, R$^2$ represents a hydrogen atom, or a straight- or branched-chain alkyl, alkenyl or alkynyl group, each such group containing up to 10 carbon atoms, and may carry one or more substituents selected from hydroxy groups, phenyl groups and cycloalkyl groups containing from 3 to 8 carbon atoms, or R$^2$ represents a cycloalkyl group containing from 3 to 8 carbon atoms, or a phenyl group which may carry one or more substituents selected from alkyl and alkoxy groups containing from 1 to 6 carbon atoms, halogen (e.g. chlorine) atoms, and nitro and trifluoromethyl groups, and R$^3$ represents a hydrogen atom, or a straight- or branched-chain alkyl, alkenyl or alkynyl group, each such group containing up to 10 carbon atoms, and may carry one or more substituents selected from hydroxy groups, phenyl groups and cycloalkyl groups containing from 3 to 8 carbon atoms, or R$^3$ represents a cycloalkyl group containing from 3 to 8 carbon atoms, or the group —NR$^2$R$^3$ represents a 5-, 6- or 7-membered heterocyclic group which may contain besides the nitrogen atom one or more additional hetero atoms (e.g. nitrogen, oxygen or sulphur) and may be substituted by one or more straight- or branched-chain alkyl groups containing from 1 to 6 carbon atoms (e.g. piperidino, 1-pyrrolidinyl and morpholino), and R$^4$ represents a hydrogen atom or a methyl or ethyl group] and pharmaceutically acceptable salts thereof.

For example, the new compounds of general formula VIII suppress the passive cutaneous anaphylactic (PCA) reaction resulting from combination of tissue-fixed reaginic antibodies with the appropriate antigenic material (termed reagin-allergen combination) and carried out in an essentially similar manner to that described by Ogilvie [Nature (Lond.), (1964), 204, 91–92; Immunology, (1967), 12, 112–131]. In the method used to test these compounds sera were obtained from rats which had been infected with larvae of the nematode parasite *Nippostrongylus brasiliensis*; as a result of the parasitic infestation reaginic antibodies are elaborated in the host mammal and are found in sera removed from such animals. Other, non-infected, rats received intradermal injections of appropriate dilutions of such sera and were then given the allergenic material along with Evans' blue dye intravenously forty-eight hours later.

The allergenic material consisted of supernatant fluid after centrifugation of homogenates of adult *Nippostrongylus brasiliensis* worms which had been macerated in Tyrode's solution. The sites of PCA reactions were visualised by the effusion of Evans' blue dye from the circulation into those areas as a result of increased capillary permeability caused by the release of biologically-active substances from cells where reagin-allergen combination had occurred. The new compounds when given intravenously to the rats just before injection of allergen, at doses of, for example, 0.001 to 2.0 mg./kg. were able to prevent the development of the reaction.

Particularly important compounds of the present invention are those of general formula VIII wherein $R^1$ represents a propoxy group, $R^2$ represents an alkyl group containing up to 10 carbon atoms and $R^3$ represents an alkyl group containing up to 4 carbon atoms, at least one of the said alkyl groups being preferably branched, for example, 8-aza-2-(5-N,N-dimethylsulphamoyl-2-propoxyphenyl)purin-6-one, 8-aza-2-(5-N,N-diethylsulphamoyl-2-propoxyphenyl)purin-6-one, 8-aza-2-(5-N,N-dipropylsulphamoyl-2-propoxyphenyl)purin-6-one, and, more especially, 8-aza-2-(5-N-isopropyl-N-methylsulphamoyl-2-propoxyphenyl)-purin-6-one, and pharmaceutically acceptable salts thereof.

Other important compounds of the present invention are those wherein $R^1$ represents a propoxy group and $R^2$ represents a substituted or unsubstituted phenyl group, for example, 8-aza-2-(5-N-phenylsulphamoyl-2-propoxyphenyl)-purin-6-one, as well as N-[3-(8-aza-6-oxopurin-2-yl)-4-propoxybenzenesulphonyl]morpholine and 8-aza-2-(5-N-cyclohexyl-N-methylsulphamoyl-2-propoxyphenyl)purin-6-one.

As a further feature of the present invention, the compounds of general formula VIII are prepared by the reaction of a compound of the general formula:

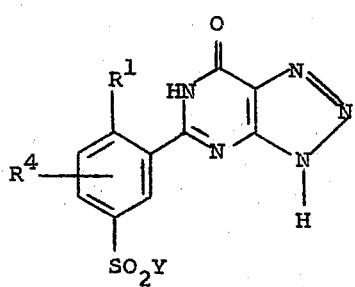

IX (wherein $R^1$ and $R^4$ are as hereinbefore defined and Y represents a halogen atom, more particularly a chlorine atom) with a compound of the general formula:

X wherein $R^2$ and $R^3$ are as hereinbefore defined.

The reaction is generally carried out at a temperature between 0° and 150°C., optionally in the presence of a solvent, for example water or an alkanol containing from 1 to 3 carbon atoms, or a mixture of such an alkanol with water, or sulpholane, and optionally in the presence of a tertiary amine, such as 1,8-bis-(dimethylamino)naphthalene or pyridine, which may also serve as a solvent. When a said tertiary amine is present the reaction is generally carried out in the absence of hydroxylic solvents such as water and alkanols.

Compounds of formula IX may be prepared from compounds of the general formula:

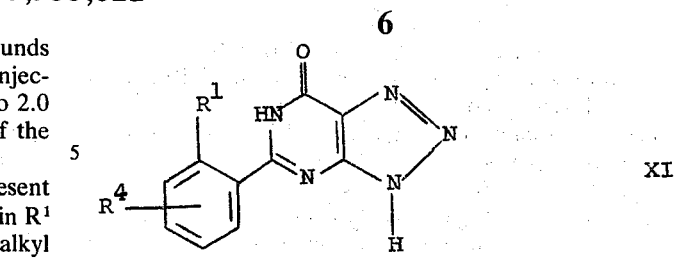

XI (wherein $R^1$ and $R^4$ are as hereinbefore defined) by the adaptation of known methods for the introduction of a group —$SO_2Y$ (wherein Y is as hereinbefore defined) on the benzene ring, for example when Y represents a chlorine atom by the action of chlorosulphonic acid at or near 0°C.

The compounds of formula XI may be prepared as described in our aforementioned specification.

The present invention includes pharmaceutically acceptable salts of compounds of general formula VIII with pharmaceutically acceptable bases. By the term "pharmaceutically acceptable salts" is meant salts the cations of which are relatively innocuous to the animal organism when used in therapeutic doses so that the beneficial pharmacological properties of the parent compounds are not vitiated by side effects ascribable to those cations. Suitable salts include the alkali metal, e.g. sodium and potassium, and ammonium salts and salts of amines known in the art to be pharmaceutically acceptable, e.g. ethylene diamine, choline, diethanolamine, triethanolamine, octadecylamine and 1-(3,4-dihydroxyphenyl)-2-isopropylaminoethanol.

Pharmaceutically acceptable salts may be prepared by the reaction together of stoichiometric quantities of a compound of general formula VIII and the appropriate base, that is to say, a base as described immediately hereinbefore, for example at an elevated temperature, with or without an appropriate solvent, preferably followed by recrystallisation from an appropriate solvent, for example a hydroxylic solvent, e.g. an alkanol, of the salt so formed.

The following Examples illustrate the preparation of the new compounds of the present invention.

EXAMPLE 1

8-Aza-2-(5-chlorosulphonyl-2-propoxyphenyl)-purin-6-one (3.7 g.) was dissolved at room temperature in a stirred solution of dimethylamine in ethanol (75 ml.; 33% w/v) and the solution was stirred for a further 90 minutes, then heated on the steam-bath for 10 minutes. The more volatile components were removed in vacuo to give an oil, which was treated with water (50 ml.) containing a few drops of the ethanolic dimethylamine solution, filtered, and the filtrate acidified to pH 1 by means of concentrated hydrochloric acid. The white crystalline precipitate was recrystallised from aqueous ethanol and dried at 140°C./10 mm.Hg to give 8-aza-2-(5-N,N-dimethylsulphamoyl-2-propoxyphenyl)purin-6-one (2.45 g.), m.p. 227°–229°C.

By proceeding in a similar manner (except where a different reaction period is indicated), but substituting for the ethanolic dimethylamine the appropriate quantities of the following solutions:
aqueous methylamine (25% w/v),
aqueous ammonia (specific gravity 0.880),
aqueous t-butylamine (33% w/v) (24 hours reaction period),
aqueous ethylamine (35% w/v), aqueous 2-methylamino)ethanol (30% w/v),
aqueous 1-deoxy-1-(methylamino)glucitol (50% w/v) (24 hours reaction period),
aqueous 1-amino-1-deoxyglucitol (50% w/v) (24 hours reaction period),
aqueous pyrrolidine (30% w/v),
hexylamine (30% w/v solution in 50% w/v aqueous ethanol) (210 minutes reaction period),
aqueous N-methyl-butylamine (30% w/v) (24 hours reaction period),
aqueous diethylamine (30% w/v) (24 hours reaction period),
aqueous N-methyl-isopropylamine (40% w/v) (24 hours reaction period),
ethanolic N-methyl-benzylamine (12% w/v) (24 hours reaction period),
ethanolic N-methyl-cyclohexylamine (33% w/v) (24 hours reaction period),
and dipropylamine (33% w/v solution in 50% w/v aqueous ethanol) (24 hours reaction period),
there were prepared:
8-aza-2-(5-N-methylsulphamoyl-2-propoxyphenyl)-purin-6-one, m.p. 227°–228°C. (after removing ethanol of crystallisation by dissolving in hot 2N aqueous ammonia, reprecipitating by means of concentrated hydrochloric acid, and drying at 140°C. /10 mm.Hg),
8-aza-2-(2-propoxy-5-sulphamoylphenyl)purin-6-one, m.p. 271°–272°C. (recrystallised from acetic acid), 8-aza-2-(5-N-t-butylsulphamoyl-2-propoxyphenyl)purin-6-one, m.p. 240°–242°C.,
8-aza-2-(5-N-ethylsulphamoyl-2-propoxyphenyl)purin-6-one, m.p. 240°–241°C. (recrystallised from ethanol),
8-aza-2-[5-(N-2-hydroxyethyl-N-methylsulphamoyl)-2-propoxyphenyl]purin-6-one, m.p. 216°–217°C. (recrystallised from ethanol),
N-[3-(8-aza-6-oxopurin-2-yl)-4-propoxybenzenesulphonyl]-1-deoxy-1-methylaminoglucitol, m.p. 183.5°–185°C. (recrystallised from water), N-[3-(8-aza-6-oxopurin-2-yl)-4-propoxybenzenesulphonyl]-1-amino-1-deoxyglucitol, m.p. 205°–207.5°C. (recrystallised from water),
N-[3-(8-aza-6-oxopurin-2-yl)-4-propoxybenzenesulphonyl]purrolidine, m.p. 250°–251°C. (recrystallised from ethanol),
8-aza-2-(5-N-hexylsulphamoyl-2-propoxyphenyl)purin-6-one, m.p. 153°–155°C. (recrystallised from methanol and dried at 100°C./10 mm.Hg),
8-aza-2-(5-N-butyl-N-methylsulphamoyl-2-propoxyphenyl)-purin-6-one, m.p. 178°–179°C., 8-aza-2-(5-N,N-diethylsulphamoyl-2-propoxyphenyl)purin-6-one, m.p. 228°–229°C. (purified by dissolving in hot 2N aqueous ammonia and reprecipitating by means of concentrated hydrochloric acid),
8-aza-2-(5-N-isopropyl-N-methylsulphamoyl-2-propoxyphenyl)purin-6-one, m.p. 257.5°–258°C. (recrystallised from acetonitrile),
8-aza-2-(5-N-benzyl-N-methylsulphamoyl-2-propoxyphenyl)-purin-6-one, m.p. 132°–133°C. (recrystallised from ethanol),
8-aza-2-(5-N-cyclohexyl-N-methylsulphamoyl-2-propoxyphenyl)purin-6-one, m.p. 216°–217°C., and 8-aza-2-(5-N,N-dipropylsulphamoyl-2-propoxyphenyl)-purin-6-one, m.p. 110°–114°C. (recrystallised from aqueous acetic acid, and containing one molecule of acetic acid of crystallisation per molecule), respectively.

By again proceeding in a similar manner, but substituting 8-aza-2-(5-chlorosulphonyl-2-methoxyphenyl)-purin-6-one for the 8-aza-2-(5-chlorosulphonyl-2-propoxyphenyl)purin-6-one used as a starting material, there was prepared 8-aza-2-(5-N,N-dimethylsulphamoyl-2-methoxyphenyl)purin-6-one, m.p. 266°–267°C.

By again proceeding in a similar manner, using 8-aza-2-(5-chlorosulphonyl-2-methoxyphenyl)purin-6-one as starting material, but replacing the ethanolic dimethylamine by the appropriate quantities of the following solutions:
aqueous isopropylamine (33% w/v),
aqueous t-butylamine (33% w/v),
aqueous N-methyl-isopropylamine (40% w/v),
there were prepared:
8-aza-2-(5-N-isopropylsulphamoyl-2-methoxyphenyl)-purin-6-one, m.p. 274°–275°C. (recrystallised from aqueous acetic acid),
8-aza-2-(5-N-t-butylsulphamoyl-2-methoxyphenyl)-purin-6-one, m.p. 233°–235°C. (recrystallised from aqueous acetic acid), and
8-aza-2-(5-N-isopropyl-N-methylsulphamoyl-2-methoxyphenyl)purin-6-one, m.p. 223°–225°C. (purified by dissolving in hot 2N aqueous ammonia and reprecipitating by means of concentrated hydrochloric acid), respectively.

The 8-aza-2-(5-chlorosulphonyl-2-propoxyphenyl)-purin-6-one, used as starting material in the above preparations, was obtained in the following manner:
8-Aza-2-(2-propoxyphenyl)purin-6-one (5.0 g.; prepared as described in Example 1 of our above-mentioned specification) was gradually dissolved in stirred chlorosulphonic acid (35 ml.) at a temperature between 0° and 5°C. The mixture was allowed to stand at that temperature for 48 hours and then added slowly to ice (150 g.), still maintaining the temperature at between 0° and 5°C. The precipitate was filtered off, washed well with ice-cold water and dried in a desiccator to give 8-aza-2-(5-chlorosulphonyl-2-propoxyphenyl)purin-6-one (6.0 g.), sufficiently pure for use in the next stage without further purification being necessary.

By proceeding in a similar manner, 8-aza-2-(5-chlorosulphonyl-2-methoxyphenyl)purin-6-one was prepared from 8-aza-2-(2-methoxyphenyl)purin-6-one (which was itself prepared as described in Example 1 of our aforementioned specification).

EXAMPLE 2

8-Aza-2-(5-chlorosulphonyl-2-propoxyphenyl)purin-6-one (3.7 g.; prepared as described in Example 1) was added to a stirred solution of benzylamine (5ml.) in dry ethanol (50 ml.) at room temperature. The mixture was stirred for a further 2 hours at room temperature and then heated at reflux for 1 hour. The mixture was cooled and the precipitated solid stirred in 2N hydrochloric acid at 60°C. for 30 minutes. The mixture was cooled to room temperature and the solid was filtered off, recrystallised from methanol with the aid of charcoal, and dried at 100°C./10 mm.Hg to give 8-aza-2-(5-N-benzylsulphamoyl-2-propoxyphenyl)purin-6-one (2.74 g.), m.p. 150°–151°C.

EXAMPLE 3

A mixture of morpholine (50 ml.) and 8-aza-2-(5-chlorosulphonyl-2-propoxyphenyl)purin-6-one (3.7 g.)

was stirred and heated at reflux for 90 minutes. Excess morpholine was then removed in vacuo, and the residue was dissolved in hot 2N aqueous ammonia solution, insoluble material filtered off, and the solution then acidified to pH 1 by means of concentrated hydrochloric acid. The precipitated solid obtained was recrystallised from ethanol and dried at 140°C./10 mm.Hg to give N-[3-(8-aza-6-oxopurin-2-yl)-4-propoxybenzenesulphonyl]morpholine (2.28 g.), m.p. 248°–249°C.

By proceeding in a similar manner, but substituting the appropriate quantity of piperidine for the morpholine used as a starting material, there was prepared N-[3-(8-aza-6-oxopurin-2-yl)-4-propoxybenzenesulphonyl]piperidine, m.p. 270°–271°C. (recrystallised from aqueous ethanol).

EXAMPLE 4

8-Aza-2-(5-chlorosulphonyl-2-propoxyphenyl)-purin-6-one (2.5 g.) was added slowly to a solution of pure N-methylaniline (1.5 g.) in dry pyridine (50 ml.) at 0°C. After stirring at this temperature for 2 hours, the mixture was stirred for a further 24 hours at room temperature. The precipitated solid was then filtered off and stirred in hydrochloric acid (2N; 50 ml.) for 1 hour. The resulting white solid was then recrystallised from aqueous acetic acid and dried at 140°C./10 mm.Hg to give 8-aza-2-(5-N-methyl-N-phenylsulphamoyl-2-propoxyphenyl)purin-6-one (1.2 g.), m.p. 250°–251°C.

By proceeding in a similar manner, but substituting the appropriate quantity of aniline for the N-methylaniline used as starting material, there was prepared 8-aza-2-(5-N-phenylsulphamoyl-2-propoxyphenyl)-purin-6-one, m.p. 253°–254°C. (recrystallised from aqueous acetic acid).

EXAMPLE 5

8-Aza-2-(5-chlorosulphonyl-2-propoxyphenyl)-purin-6-one (3.7 g.), was suspended in dry pyridine (50 ml.) and then treated with o-anisidine (5.0 g.). This mixture was then stirred and heated at 60°C. for 24 hours. The resulting mixture was then evaporated to dryness in vacuo and treated with hydrochloric acid (2N; 100 ml.). After cooling in ice, a solid gradually formed from the oil. This solid was then dissolved in dilute ammonia solution and then the pH was adjusted to pH 8 by means of concentrated hydrochloric acid. After filtration to remove any precipitated solid the pH of the filtrate was adjusted to pH 1 with concentrated hydrochloric acid. The resulting solid was then treated again with ammonia followed by concentrated hydrochloric acid to give 8-aza-2-[5-N-(2-methoxyphenyl)-sulphamoyl-2-propoxyphenyl]purin-6-one (0.65 g.), m.p. 139°–142°C.

By proceeding in a similar manner, but substituting the appropriate quantities of m-anisidine, p-anisidine and 3-trifluoromethylaniline for the o-anisidine used as starting material, there were prepared:

8-aza-2-[5-N-(3-methoxyphenyl)sulphamoyl-2-propoxyphenyl]purin-6-one, m.p. 137°–139°C.,
8-aza-2-[5-N-(4-methoxyphenyl)sulphamoyl-2-propoxyphenyl]purin-6-one, m.p. 150°–152°C., and
8-aza-2-[5-N-(3-trifluoromethylphenyl)sulphamoyl-2-propoxyphenyl]purin-6-one, m.p. 150°–152°C., respectively.

EXAMPLE 6

8-Aza-2-(5-chlorosulphonyl-2-propoxyphenyl)-purin-6-one (3.7 g.) was added slowly with stirring to a solution of dihexylamine (30 ml.) in ethanol (30 ml.). The mixture was stirred for 24 hours at room temperature and then the ethanol was removed in vacuo. The resulting oil was then diluted with petroleum ether (b.p. 40°–60°C.) (250 ml.), the precipitated solids being filtered off and washed with a further quantity of petroleum ether. These solids were then dissolved in aqueous sodium hydroxide solution (2N) and this solution was extracted with petroleum ether (b.p. 40°–60°C.) (3 × 50 ml.). The aqueous layer was then acidified to pH 1 with concentrated hydrochloric acid and the resultant suspension was shaken with chloroform (100 ml.). Any solid remaining undissolved was then filtered off, the organic layer was separated, washed with water (2 × 20 ml.) and dried over sodium sulphate. After removal of the chloroform there was obtained an oil which, on scratching, solidified and was then recrystallised from aqueous ethanol to give 8-aza-2-(5-N,N-dihexylsulphamoyl-2-propoxyphenyl)purin-6-one (0.9 g.), m.p. 126.5°–128.5°C.

EXAMPLE 7

Fresh 8-aza-2-(5-chlorosulphonyl-4-methyl-2-propoxyphenyl)purin-6-one (7.7 g.) was added slowly to a stirred solution of methylamine in ethanol (180 ml.; 33% w/v), the mixture was stirred at room temperature for 210 minutes and then heated on the steam bath for 10 minutes. The solution was evaporated to dryness, the residue was suspended in water and sufficient aqueous methylamine solution (40% w/v) was added so as to give a clear solution. The solution was then treated with charcoal, filtered, cooled in ice and acidified to pH 1 with concentrated hydrochloric acid. The light yellow solid formed was filtered off, washed with water and recrystallised from isopropanol to give 8-aza-2-(4-methyl-5-N-methylsulphamoyl-2-propoxyphenyl)purin-6-one (6.78 g.), m.p. 254°–257°C. (with decomposition). A sample (1.5 g.) of this material was further purified by dissolving in dilute aqueous ammonia solution, filtering, and acidification with glacial acetic acid. The acid mixture was heated to give a clear solution and then allowed to cool to give crystals of 8-aza-2-(4-methyl-5-N-methylsulphamoyl-2-propoxyphenyl)purin-6-one (1.2 g.), m.p. 259°–260°C. (with decomposition).

By proceeding in a similar manner, but replacing the ethanolic methylamine solution, used as a starting material, by the appropriate quantities of the following solutions:
ethanolic dimethylamine (25% w/v),
aqueous ammonia (specific gravity 0.880), and
aqueous t-butylamine (33% w/v),
there were prepared:
8-aza-2-(4-methyl-5-N,N-dimethylsulphamoyl-2-propoxyphenyl)purin-6-one, m.p. 256°–257°C.,
8-aza-2-(4-methyl-2-propoxy-5-sulphamoylphenyl)-purin-6-one, m.p. 299°–300°C. (with decomposition) from ethanol, and
8-aza-2-(5-N-t-butylsulphamoyl-4-methyl-2-propoxyphenyl)purin-6-one, m.p. 233°–235°C.

The 8-aza-2-(5-chlorosulphonyl-4-methyl-2-propoxyphenyl)purin-6-one, used as a starting material, was prepared as follows:

8-Aza-2-(4-methyl-2-propoxyphenyl)purin-6-one (28.5 g.) was dissolved, with stirring, in chlorosulphonic acid (150 ml.) at 0°C. and maintained at 0°C. in a sealed vessel for 40 hours. The mixture was then cautiously added dropwise to a mixture of ice and water (500 ml.) with external cooling so as to maintain the temperature at below 3°C. After stirring for a further 10 minutes, the 8-aza-2-(5-chlorosulphonyl-4-methyl-2-propoxyphenyl)-purin-6-on (32 g.) was filtered off, washed well with water, and dried in vacuo over phosphorus pentoxide.

The 8-aza-2-(4-methyl-2-propoxyphenyl)purin-6-one (m.p. 213°–215°C.) was prepared from 4-methylsalicylamide by the application and adaptation of methods described in our aforementioned specification, via
4-methyl-2-propoxybenzamide, m.p. 140°–141°C.,
4-methyl-2-propoxybenzamidine hydrochloride,
6-amino-2-(4-methyl-2-propoxyphenyl)-5-nitrosopyrimid-
4-one, m.p. 229°–234°C., and
5,6-diamino-2-(4-methyl-2-propoxyphenyl)pyrimid-
4-one, m.p. 182°–183°C.

The 4-methylsalicylamide, m.p. 184°–186°C., was prepared from methyl 4-methylsalicylate (Behal and Tiffeneau, Bull, Soc. Chim. France., 1908 [4], 3, 730) by adaptation of the method described by Goldbeck, Ber. dtsch. Chem. Ges. 1891, 24, 3659, for the preparation of 5-methylsalicylamide.

EXAMPLE 8

A mixture of 8-aza-2-(5-chlorosulphonyl-2-propoxyphenyl)purin-6-one (1.85 g.), N-ethyl-isopropylamine (0.87 g.) and 1,8-bis(dimethylamino)naphthalene (1.07 g.) in dry sulpholane (15 ml.) was stirred and heated at 60°C. overnight. The mixture was then cooled and added to hydrochloric acid (25% w/w, 100 ml.). The precipitated solid was filtered off, washed well with water, and stirred with aqueous sodium carbonate solution (N; 100 ml.) for 10 minutes. After removal of undissolved material by filtration, the filtrate was acidified with concentrated hydrochloric acid, and the resulting precipitated solid was filtered off and washed well with boiling water followed by cold water. The solid was dissolved in 2N aqueous sodium hydroxide solution, and the solution washed with petroleum ether (b.p. 40°–60°C.). The aqueous layer was acidified with hydrochloric acid, the precipitated solid was extracted into ethyl acetate, the extract was washed with water, dried and evaporated. The residue was dissolved in aqueous ammonia and precipitated again by treatment with hydrochloric acid.

Recrystallisation from aqueous acetic acid gave 8-aza-2-(5-N-ethyl-N-isopropylsulphamoyl-2-propoxyphenyl)purin-6-one (0.17 g.), m.p. 154°–157°C.

By proceeding in a similar manner, but substituting the appropriate quantity of n-sec.-butylmethylamine for the N-ethyl-isopropylamine used as starting material, there was prepared 8-aza-2-(5-N-sec.-butyl-N-methylsulphamoyl-2-propoxyphenyl)purin-6-one, m.p. 224°C. (recrystallised from isopropanol).

EXAMPLE 9

8-Aza-2-(5-chlorosulphonyl-2-propoxyphenyl)-purin-6-one (3.7 g.) was added slowly with cooling and stirring to aqueous isopropylamine 933% w/w; 50 ml.). The mixture was stirred for 3 hours at room temperature, and evaporated under reduced pressure. The residue was suspended in water (50 ml.), isopropylamine (5 ml.) was added, and the mixture was heated on the steam bath until a solution was obtained. The solution was acidified with concentrated hydrochloric acid and the precipitated solid was filtered off, washed with water, dried and recrystallised from aqueous acetic acid to give 8-aza-2-(5-N-isopropylsulphamoyl-2-propoxyphenyl)purin-6-one (2.0 g.), m.p. 272°–274°C. (with decomposition).

EXAMPLE 10

2,6-Dimethylaniline (2.5 g.) was added to a stirred suspension of 8-aza-2-(5-chlorosulphonyl-2-propoxyphenyl)purin-6-one (1.85 g.) in dry pyridine (40 ml.) and the mixture was stirred and heated at reflux for 20 hours. The solvent was then removed in vacuo and the residue was treated with hydrochloric acid (2N; 100 ml.) and heated with stirring on the steam bath for 5 minutes. On cooling, the gum that separated turned gradually to a solid which, on crystallisation (with charcoaling) from isopropanol, gave 8-aza-2-[5-N-(2,6-dimethylphenyl)-sulphamoyl-2-propoxyphenyl]purin-6-one (1.04 g.), m.p. 240°–242°C.

EXAMPLE 11

A mixture of 8-aza-2-(5-chlorosulphonyl-2-propoxyphenyl)purin-6-one (1.85 g.), 4-chloroaniline (1.28 g.) and 1,8-bis9dimethylamino)naphthalene (1.07 g.) in dry sulpholane (10 ml.) was stirred and heated at 110°–115°C. for 20 hours. The mixture was then poured into hydrochloric acid (2N; 100 ml.) and cooled, to give a dark tar. Most of this tar was then dissolved in hot aqueous ammonia (2N; 100 ml.) and, after charcoaling, was reprecipitated by addition of concentrated hydrochloric acid. This base/acid purification procedure was repeated, and finally recrystallisation from aqueous acetic acid gave 8-aza-2-[5-N-(4-chlorophenyl)sulphamoyl-2-propoxyphenyl]purin-6-one (0.67 g.), m.p. 157°–164°C.

By proceeding in a similar manner, but substituting the appropriate quantity of 4-nitroaniline for the 4-chloroaniline used as starting material, there was prepared 8-aza-2-[5-N-(4-nitrophenyl)sulphamoyl-2-propoxyphenyl]purin-6-one, m.p. 170°–174°C.

EXAMPLE 12

A mixture of 8-aza-2-(5-N-methylsulphamoyl-2-propoxyphenyl)purin-6-one (0.36 g.; prepared as described in Example 1) and triethanolamine (0.16 g.) in dry ethanol (15 ml.) was heated at reflux until solution occurred. The crystalline mass formed on cooling was filtered off, washed with dry ethanol, and recrystallised from dry ethanol to give the triethanolamine salt of 8-aza-2-(5-N-methylsulphamoyl-2-propoxyphenyl)purin-6-one (0.3 g.), m.p. 164°–166°C. (with decomposition).

The present invention includes within its scope pharmaceutical compositions which comprise one or more compounds of general formula VIII, or a pharmaceutically acceptable salt thereof, in association with a pharmaceutical carrier or coating. In clinical practice the compounds of the present invention will normally be administered orally, sub-lingually, nasally, rectally or parenterally.

Solid compositions for oral administration include compressed tablets, pills, dispersible powders, and granules. In such solid compositions the active compound or compounds is or are mixed with at least one inert diluent such as calcium carbonate, potato starch, alginic acid, or lactose. The compositions may also comprise, as is normal practice, additional substances other than inert diluents, e.g. lubricating agents, such as magnesium stearate. Liquid compositions for oral administration include pharmaceutically acceptable emulsions, solutions, suspensions, and elixirs containing inert diluents commonly used in the art, such as water and liquid paraffin. Besides inert diluents such compositions may also comprise adjuvants, such as wetting and suspending agents, and sweetening, flavouring, perfuming and preserving agents. The compositions according to the invention, for oral administration, also include capsules of absorbable material such as gelatin containing the active compound or compounds with or without the addition of diluents or excipients.

The compound(s) may also be administered sub-lingually by administration of relatively slowly dissolving tablets which, besides including inert diluents as commonly used in the art, may contain sweetening, flavouring, perfuming and preserving agents.

Solid compositions for rectal administration include suppositories formulated in manner known per se and containing the active compound or compounds.

Preparations according to the invention for parenteral administration include sterile aqueous or non-aqueous solutions, suspensions, or emulsions. Examples of non-aqueous solvents or suspending media are propylene glycol, polyethylene glycol, vegetable oils such as olive oil, and injectable organic esters such as ethyl oleate. These compositions may also contain adjuvants such as preserving, wetting, emulsifying and dispersing agents. They may be sterilised, for example, by filtration through a bacteria-retaining filter, by incorporation of sterilising agents in the compositions, by irradiation, or by heating. They may also be manufactured in the form of sterile solid compositions, which can be dissolved in sterile water or some other sterile injectable medium immediately before use.

The percentage of active ingredient in the compositions of the invention may be varied, it being necessary that it should constitute a proportion such that a suitable dosage for the therapeutic effect desired shall be obtained. Obviously several unit dosage forms may be administered at about the same time. Generally, the compositions should contain 0.1% to 50% by weight of azapurinone compound, especially when in tablet form. When in aerosol form as hereinafter described the compositions should contain 0.2 to 5%, preferably 2 to 5%, by weight of azapurinone compound.

The active compound or compounds may also be administered by methods known for the inhalation of drugs which are not themselves gaseous under normal conditions of administration. Thus, a solution of the compound or compounds in a suitable pharmaceutically acceptable solvent, for example water, can be nebulized by a mechanical nebulizer, for example a Wright Nebulizer, to given an aerosol of finelydivided liquid particles suitable for administration for inhalation orally or nasally. The solution may contain stabilizing agents and buffering agents to give it an isotonic character, e.g. sodium chloride, sodium citrate and citric acid.

The compound or compounds may also be administered orally or nasally by inhalation in the form of aerosols generated from self-propelling pharmaceutical compositions. Compositions suitable for this purpose may be obtained by dissolving or suspending in finelydivided form, preferably micronized to an average particle size of less than 5 microns, the active compound or compounds in pharmaceutically acceptable solvents, e.g. ethanol, which are co-solvents assisting in dissolving the compound or compounds in the volatile liquid propellant hereinafter described, or pharmaceutically acceptable suspending or dispersing agents, for example aliphatic alcohols such as oleyl alcohol, Span/85 and isopropyl myristate, and incorporating the solutions or suspensions obtained with pharmaceutically acceptable volatile liquid propellants, in conventional pressurized packs which may be made of any suitable material, e.g. metal, plastics or glass, adequate to withstand the pressures generated by the volatile propellants in the pack. Pressurized pharmaceutically acceptable gases, such as nitrogen, may also be used as propellants. The pressurized pack is preferably fitted with a metered valve which dispenses a controlled quantity of the self-propelling aerosol composition as a single dose.

Suitable volatile liquid propellants are known in the art and include fluorochlorinated alkanes containing from one to four, and preferably one or two, carbon atoms, for example dichlorodifluoromethane, dichlorotetrafluoroethane, trichloromonofluoromethane, dichloromonofluoromethane and monochlorotrifluoromethane. Preferably, the vapour pressure of the volatile liquid propellant is between about 25 to 65 pounds, and more especially between about 30 and 55 pounds, per square inch gauge at 21°C. As is well-known in the art, volatile liquid propellants of different vapour pressures may be mixed in varying proportions to give a propellant having a vapour pressure appropriate to the production of a satisfactory aerosol and suitable for the chosen container. For example dichlorodifluoromethane (vapour pressure 85 pounds per square inch gauge at 21°C.) and dichlorotetrafluoroethane (vapour pressure 28 pounds per square inch gauge at 21°C.) may be mixed in varying proportions to give propellants having vapour pressures intermediate between those of the two constituents, e.g. a mixture of dichlorodifluoromethane and dichlorotetrafluoroethane in the proportions 38:62 respectively by weight has a vapour pressure of 53 pounds per square inch gauge at 21°C.

The self-propelling pharmaceutical compositions may be prepared by dissolving the required quantity of the compound or compounds in the co-solvent or combining the required quantity of the compound with a measured quantity of suspending or dispersing agent. A measured quantity of this composition is then placed in an open container which is to be used as the pressurized pack. The container and its contents are then cooled below the boiling temperature of the volatile propellant to be used. The required quantity of liquid propellant, cooled below its boiling temperature, is then added and the contents of the container mixed. The container is then sealed with the required valve fitting without allowing the temperature to rise above the boiling temperature of the propellant. The temperature of the sealed container is then allowed to rise to ambient temperature with shaking to ensure complete homogeneity of the contents to give a pressurized pack suitable for generating aerosols for inhalation. Alternatively, the co-solvent solution of the compound or compounds or combination of compound or compounds and suspending or dispersing agent is placed in the open container, the container sealed with a valve, and the liquid propellant introduced under pressure.

Means for producing self-propelling compositions for generating aerosols for the administration of medicaments are, for example, described in detail in U.S. Pat. Nos. 2,868,691 and 3,095,355.

The compound or compounds may also be administered orally by inhalation in the form of a dry micronised powder, which may be diluted with one or more suitable pharmaceutically acceptable inert solid diluents selected from, for example, lycopodium, boric acid, starch, bismuth subcarbonate and heavy magnesium carbonate.

The pharmaceutical compositions of the present invention may contain, in addition to the compound or compounds of formula VIII, one or more substances known per se to have bronchodilating actions in man, for example, isoprenaline, salbutamol and prostaglandin $E_1$ ($PGE_1$).

By the term "pharmaceutically-acceptable" as applied in this specification to solvents, suspending or dispersing agents, propellants, gases and solid diluents is meant solvents, suspending or dispersing agents, propellants, gases and solid diluents which are non-toxic when used in aerosols suitable for the inhalation therapy.

It is highly desirable that the aerosols or micronised powders should have a particle size less than about 10 microns and preferably less than 5 microns, for example, between 0.5 and 3 microns, to ensure effective distribution to very narrow bronchioles. Preferably, administration is by means of devices enabling controlled quantities of the active ingredients to be administered, for example by means of the metered valves hereinbefore mentioned.

The dose of the compounds of general formula VIII employed depends upon the desired therapeutic effect, the route of administration and the duration of the treatment. In the adult, the doses are generally between 0.002 and 0.4 mg./kg. body weight per day by administration by inhalation in divided doses.

The following Example illustrates pharmaceutical compositions according to the present invention.

EXAMPLE 13

Micromilled triethanolamine salt of 8-aza-2-(5-N-methylsulphamoyl-2-propoxyphenyl)purin-6-one (100 mg.) and oleyl alcohol (200 mg.) were placed in a polyvinyl chloride-coated glass bottle (20 ml. capacity) and filled with a mixture of dichlorodifluoromethane and dichlorotetrafluoroethane to give a total volume of 7.1 ml. The bottle was sealed with a metered valve (with dip tube) delivering 0.1 ml doses. Each puff (generated from 0.1 ml. of solution) of aerosol released from the pressurized pack thus obtained contained 1 mg. of 8-aza-2-(5-N-methylsulphamoyl-2-propoxyphenyl)purin-6-one [in terms of the free 8-aza-2-(5-N-methylsulphamoyl-2-propoxyphenyl)purin-6-one].

We claim:

1. An 8-azapurin-6-one derivative of the formula:

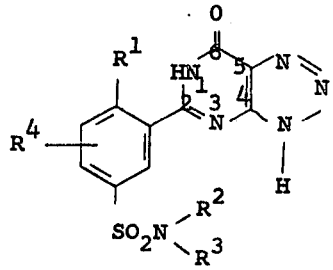

wherein $R^1$ represents hydroxy, or alkoxy or alkylthio each containing 1 to 10 carbon atoms, $R^2$ represents hydrogen, alkyl of 1 to 10 carbon atoms, alkyl of 1 to 10 carbon atoms carrying one or more substituents selected from the group consisting of hydroxy and phenyl, cycloalkyl containing 3 to 8 carbon atoms, phenyl, or phenyl carrying one or more substituents selected from the group consisting of alkyl or alkoxy each containing 1 to 6 carbon atoms, halogen, nitro and trifluoromethyl, $R^3$ represents hydrogen, alkyl of 1 to 10 carbon atoms, or alkyl of 1 to 10 carbon atoms carrying one or more substituents selected from the group consisting of hydroxy and phenyl, or cycloalkyl containing 3 to 8 carbon atoms, and $R^4$ represents hydrogen, methyl or ethyl, or a pharmaceutically acceptable salt thereof.

2. An 8-azapurin-6-one derivative according to claim 1 wherein $R^1$ represents hydroxy, or alkoxy or alkylthio each containing 1 to 10 carbon atoms, $R^2$ and $R^3$ each represent hydrogen, alkyl of 1 to 10 carbon atoms, or alkyl of 1 to 10 carbon atoms carrying one or more hydroxy groups, and $R^4$ represents hydrogen, or a pharmaceutically acceptable salt thereof.

3. An 8-azapurin-6-one derivative according to claim 1 wherein $R^1$ represents propoxy, $R^2$ represents phenyl, or phenyl carrying one or more substituents selected from the group consisting of alkyl or alkoxy each containing 1 to 6 carbon atoms, halogen, nitro and trifluoromethyl, $R^3$ represents hydrogen, alkyl of 1 to 10 carbon atoms, or alkyl of 1 to 10 carbon atoms carrying one or more substituents selected from the group consisting of hydroxy and phenyl, or cycloalkyl containing 3 to 8 carbon atoms, and $R^4$ represents hydrogen, methyl or ethyl, or a pharmaceutically acceptable salt thereof.

4. An 8-azapurin-6-one derivative according to claim 1 wherein $R^1$ represents alkoxy containing 1 to 3 carbon atoms, or a pharmaceutically acceptable salt thereof.

5. An 8-azapurin-6-one derivative according to claim 1 wherein $R^1$ represents propoxy, $R^2$ represents alkyl containing 1 to 10 carbon atoms, $R^3$ represents alkyl containing 1 to 4 carbon atoms, and $R^4$ represents hydrogen, methyl or ethyl or a pharmaceutically acceptable salt thereof.

6. An 8-azapurin-6-one derivative according to claim 5 wherein one or both of the alkyl groups represented by $R^2$ and $R^3$ is branched-chain alkyl.

7. The azapurinone according to claim 1 which is 8-aza-2-(5-N,N-dimethylsulphamoyl-2-propoxyphenyl)purin-6-one, or a pharmaceutically acceptable salt thereof.

8. The azapurinone according to claim 1 which is 8-aza-2-(5-N,N-diethylsulphamoyl-2-propoxyphenyl)-purin-6-one, or a pharmaceutically acceptable salt thereof.

9. The azapurinone according to claim 1 which is 8-aza-2-(5-N,N-dipropylsulphamoyl-2-propoxyphenyl)purin-6-one, or a pharmaceutically acceptable salt thereof.

10. The azapurinone according to claim 1 which is 8-aza-2-(5-N-isopropyl-N-methylsulphamoyl-2-propoxyphenyl)-purin-6-one, or a pharmaceutically acceptable salt thereof.

11. The azapurinone according to claim 1 which is 8-aza-2-(5-N-phenylsulphamoyl-2-propoxyphenyl)purin-6-one, or a pharmaceutically acceptable salt thereof.

12. The azapurinone according to claim 1 which is 8-aza-2-(5-N-cyclohexyl-N-methylsulphamoyl-2-propoxyphenyl)-purin-6-one, or a pharmaceutically acceptable salt thereof.

13. An azapurinone derivative according to claim 1 selected from the group consisting of 8-aza-2-(5-N-methylsulphamoyl-2-propoxyphenyl)purin-6-one, 8-aza-2-(2-propoxy-5-sulphamoylphenyl)purin-6-one, 8-aza-2-(5-N-t-butylsulphamoyl-2-propoxyphenyl)purin-6-one, 8-aza-2-(5-N-ethylsulphamoyl-2-propoxyphenyl)purin-6-one, 8-aza-2-[5-(N-2-hydroxyethyl-N-methylsulphamoyl)-2-propoxyphenyl]purin-6-one, N-[3-(8-aza-6-oxopurin-2-yl)-4-propoxybenzenesulphonyl]-1-deoxy-1-methylaminoglucitol, N-[3-(8-aza-6-oxopurin-2-yl)-4-propoxybenzenesulphonyl]-1-amino-1-deoxyglucitol, 8-aza-2-(5-N-hexylsulphamoyl-2-propoxyphenyl)purin-6-one, 8-aza-2-(5-N-butyl-N-methylsulphamoyl-2-propoxyphenyl)purin-6-one, 8-aza-2-(5-N-benzyl-N-methylsulphamoyl-2-propoxyphenyl)purin-6-one, 8-aza-2-(5-N,N-dimethylsulphamoyl-2-methoxyphenyl)purin-6-one, 8-aza-2-(5-N-isopropylsulphamoyl-2-methoxyphenyl)purin-6-one, 8-aza-2-(5-N-t-butylsulphamoyl-2-methoxyphenyl)purin-6-one, 8-aza-2-(5-N-isopropyl-N-methylsulphamoyl-2-methoxyphenyl)purin-6-one, 8-aza-2-(5-N-benzylsulphamoyl-2-propoxyphenyl)purin-6-one, 8-aza-2-(5-N-methyl-N-phenylsulphamoyl-2-propoxyphenyl)purin-6-one, 8-aza-2-[5-N-(2-methoxyphenyl)sulphamoyl-2-propoxyphenyl]-purin-6-one, 8-aza-2-[5-N-(3-methoxyphenyl)sulphamoyl-2-propoxyphenyl]purin-6-one, 8-aza-2-[5-N-(4-methoxyphenyl)-sulphamoyl-2-propoxyphenyl]purin-6-one, 8-aza-2-[5-N-(3-trifluoromethylphenyl)sulphamoyl-2-propoxyphenyl]purin-6-one, 8-aza-2-(5-N,N-dihexylsulphamoyl-2-propoxyphenyl)-purin-6-one, 8-aza-2-(4-methyl-5-N-methylsulphamoyl-2-propoxyphenyl)purin-6-one, 8-aza-2-(4-methyl-5-N,N-dimethylsulphamoyl-2-propoxyphenyl)purin-6-one, 8-aza-2-(4-methyl-2-propoxy-5-sulphamoylphenyl)purin-6-one, 8-aza-2-(5-N-t-butylsulphamoyl-4-methyl-2-propoxyphenyl)-purin-6-one, 8-aza-2-(5-N-ethyl-N-isopropylsulphamoyl-2-propoxyphenyl)purin-6-one, 8-aza-2-(5-N-sec.-butyl-N-methylsulphamoyl-2-propoxyphenyl)purin-6-one, 8-aza-2-(5-N-isopropylsulphamoyl-2-propoxyphenyl)purin-6-one, 8-aza-2-[5-N-(2,6-dimethylphenyl)sulphamoyl-2-propoxyphenyl]purin-6-one, 8-aza-2-[5-N-(4-chlorophenyl)sulphamoyl-2-propoxyphenyl]purin-6-one, 8-aza-2-[5-(4-nitrophenyl)-sulphamoyl-2-propoxyphenyl]purin-6-one, and a pharmaceutically acceptable salt thereof.

* * * * *